United States Patent [19]

Egraz et al.

[11] Patent Number: 5,278,248
[45] Date of Patent: Jan. 11, 1994

[54] WATER-SOLUBLE POLYMERS AND/OR COPOLYMERS POSSESSING INCREASED BIODEGRADABILITY, AND THEIR APPLICATIONS

[75] Inventors: Jean-Bernard Egraz, Ecully; Georges Ravet, Saint-Genis-les Ollieres; Jacky Rousset, Saint-Trivier-sur-Moignans, all of France

[73] Assignee: Coatex S.A., Genay, France

[21] Appl. No.: 974,280

[22] Filed: Nov. 10, 1992

[30] Foreign Application Priority Data

Nov. 12, 1991 [FR] France ............................ 91 14141
Nov. 12, 1991 [FR] France ............................ 91 14142

[51] Int. Cl.$^5$ ............................ C08F 8/42; C08F 8/44
[52] U.S. Cl. ............................ 525/330.2; 524/1;
524/556; 524/558; 524/599; 525/196; 525/366;
525/367; 525/375; 525/378; 525/379; 525/380;
526/317.1
[58] Field of Search ............... 525/330.2, 366, 367,
525/196, 919; 524/556

[56] References Cited

U.S. PATENT DOCUMENTS

| | | | |
|---|---|---|---|
| 4,868,228 | 9/1989 | Gonnet | 523/333 |
| 4,882,393 | 11/1989 | Herwig | 525/330.2 |
| 4,929,690 | 5/1990 | Goertz | 525/366 |
| 4,984,804 | 1/1991 | Yamada | 273/235 R |
| 5,068,151 | 11/1991 | Nakamura | 428/407 |

FOREIGN PATENT DOCUMENTS

| | | | |
|---|---|---|---|
| 0115190 | 8/1984 | European Pat. Off. | 525/330.2 |
| 3603471 | 8/1987 | Fed. Rep. of Germany . | |
| 3362 | 6/1965 | France . | |
| 0420533 | 12/1934 | United Kingdom | 525/330.2 |
| 420533 | 12/1934 | United Kingdom . | |

OTHER PUBLICATIONS

R. F. Boyd, "General Microbiology", 2nd Ed., 359 (1988) Mosby (St. Louis).
T. D. Brock, "Biology of Microorganisms", 181 (1974) Prentice Hall (New Jersey).
Chemical Abstracts, vol. 113, No. 12, Sep. 17, 1990, & JP-A-0273811, pp. 148, "Preparation of Copolymers of Acrylic Acid Metal Salts and Cyclohexanone".

Primary Examiner—Joseph L. Schofer
Assistant Examiner—Fred Zitomer
Attorney, Agent, or Firm—Oblon, Spivak, McClelland, Maier & Neustadt

[57] ABSTRACT

Water-soluble polymers and/or copolymers possessing enhanced biodegradability, and their applications are disclosed.

Acrylic and/or vinyl polymers and/or copolymers containing acid groups, in which 35% to 90% of the active acid sites are neutralized by magnesium ions, the specific viscosity is at most 25, and biodegradability is enhanced. Their decomposition after 36 days is greater than 50% as measured by the modified Sturm test.

These polymers can be used in industries as varied as: paper-making, paints, plastics, petroleum, drilling fluids, water treatment, detergents, cosmetics, textiles, inks, leather, grinding and/or splitting of minerals in water.

18 Claims, No Drawings

WATER-SOLUBLE POLYMERS AND/OR COPOLYMERS POSSESSING INCREASED BIODEGRADABILITY, AND THEIR APPLICATIONS

BACKGROUND OF THE INVENTION

1. Field of the Invention

The present invention relates to water-soluble polymers and/or copolymers with increased biodegradability.

2. Discussion of the Background

Experts are familiar with biodegradable polymers in which biodegradability results from grafting polyalkylene oxide onto acidic monomers such as acrylic acid EP0429307 and EP0430574), or from the presence of maleic anhydride accompanied by precisely-specified conditions of polymerization (EP0396303), or from terminating the polyacrylate chain with hydroxy or sulfide groups (U.S. Pat. No. 4,095,035) or with their monomeric composition (U.S. Pat. No. 4,897,458 and EP0291808).

The present invention concerns water-soluble polymers and/or copolymers, in which neutralization of active acid sites yields increased biodegradability through the use of a neutralizing agent containing magnesium ions, and biodegradable products obtained by implementing this procedure.

These polymers and/or copolymers may be used in industries as diverse as paper, paints, plastics, oil, drilling fluids, water treatment, detergents or cosmetics, textiles, inks, leathers, and grinding and/or splitting of minerals in water, etc.

In all of these fields, the solution of the problem of safeguarding the environment is becoming increasingly urgent. Thus, for ecological reasons, the expert must utilize components possessing increased biodegradability.

SUMMARY OF THE INVENTION

Accordingly, one object of the invention is to supply a polymer and/or copolymer, in particular an acrylic and/or vinyl polymer and/or copolymer possessing increased biodegradability, i.e., whose decomposition at the end of 36 days is greater than 50% by using the modified Sturm method, in order to conform optimally to environmental protection regulations (Official Journal of the EC, No. L251).

Another object of the invention is to furnish an acrylic and/or vinyl and/or copolymer possessing enhanced biodegradability and a specific viscosity of at most 25, and preferably of at most 10.

Surprisingly, the present inventors have found that the object of the invention is achieved by using, as a neutralizing agent, an agent containing magnesium ions, and, more specifically, when from 35% to 90% of the active acid sites of the acrylic and/or vinyl polymer and/or copolymer are neutralized by magnesium ions.

DETAILED DESCRIPTION OF THE PREFERRED EMBODIMENTS

These acrylic and/or vinyl polymers and/or copolymers are obtained from conventional radical polymerization procedures in the presence of polymerization regulators, such as hydroxylamine-based organic compounds and in the presence of polymerization catalysts such as peroxides and persalts, e.g., oxygenated water, persulfate, sodium hypophosphite, hypophosphorous acid.

The following monomers and/or co-monomers may be used: acrylic acid, methacrylic acid, itaconic acid, crotonic acid, fumaric acid, maleic anhydride, or, alternatively, isocrotonic acid, aconitic acid (cis or trans), mesaconic acid, sinapinic acid, undecylenic acid, angelic acid, canellic acid, or hydroxyacrylic acid, existing either as free acid or a partially neutralized salt, acrolein, acrylamide, acrylonitrile, the $C_{1-6}$ alkyl esters of acrylic and methacrylic acid, amino substituted $C_{1-6}$ alkyl esters of acrylic and methacrylic acid, and, in particular, dimethylaminoethyl methacrylate, vinylpyrrolidone, vinylcaprolactam, ethylene, propylene, isobutylene, diisobutylene, vinyl acetate, styrene, α-methylstyrene, and methyl vinyl ketone.

As suitable polymerization medium may be water, methanol, ethanol, propanol, isopropanol, the butanols, or mixtures of these, or, alternatively, dimethylformamide, dimethyl sulfoxide, tetrahydrofuran, acetone, methyl ethyl ketone, ethyl acetate, butyl acetate, hexane, heptane, benzene, toluene, xylene, mercaptoethanol, tertiododecylmercaptan, thioglycolic acid and its esters, n-dodecylmercaptan, acetic acid, tartaric acid, lactic acid, citric acid, gluconic acid, glucoheptonic acid, 2-mercaptopropionic acid, thiodiethanol, halogenated solvents such as carbon tetrachloride, chloroform, methylene chloride, and monopropylene glycol or diethylene glycol ethers or mixtures of these latter.

The solution of the acid polymerization product thus obtained is potentially neutralized, partially or completely, to a degree of 35% to 90% using a neutralizing agent containing magnesium ions, and, optionally, using a neutralizing agent containing monovalent ions. The degree of neutralization by magnesium is preferably 35%–60% when up to 65% of the active acid sites are neutralized by a monovalent ion. The degree of neutralization by magnesium is preferably 60%–90% when up to 40% of the active acid sites are neutralized by a monovalent ion.

The monovalent neutralizing agent may be chosen from the group comprising the alkali cations (e.g., sodium, lithium, and potassium), ammonium, the primary, secondary, or tertiary aliphatic and/or cyclic amines (e.g., the ethanolamines (mono-, di-, and tri-ethanolamine), mono- and di-ethylamine, cyclohexylamine, and methyl cyclohexylamine). Of these monovalent ions, sodium is preferred. In a preferred embodiment the aliphatic amine contains an aliphatic substituent of 1–20 carbon atoms, preferably 1–6 carbon atoms. In another preferred embodiment the cyclic portion of the cyclic amine contains 3–20 carbon atoms, preferably 4–7 carbon atoms.

In a preferred embodiment, 50% of the active acid sites are neutralized by magnesium and 50% are neutralized by sodium. In another preferred embodiment, 75% are neutralized by magnesium and 25% by sodium. In another preferred embodiment, 88% are neutralized by magnesium and 12% by sodium.

The solution of the polymerization product, whether acidic or neutralized in this manner, can also be treated using static or dynamic procedures known to the artisan and calling for the use of one or several polar solvents belonging, in particular, to the group comprising methanol, ethanol, propanol, isopropanol, butanols, acetone, and tetrahydrofuran, thus giving a two-phase separation, each of which is collected separately. Further, the polymer may be formed by grafting acrylic and/or vinyl monomers onto a polyalkylene glycol-based substrate.

The less dense phase contains the main fraction of the polar solvent, and forms the fraction of the polymer and/or copolymer having low molecular weight, while the denser aqueous phase forms the polymer and/or copolymer fraction having the higher molecular weight.

The polymers and/or copolymers according to the invention generally have a specific viscosity of at most 25, and preferably of at most 10.

These polymers may be used in conjunction with suitable additives in many varied compositions such as in paper, paints, plastics, oil, drilling fluids, water treatment, detergents or cosmetics, textiles, inks, leathers, and grinding and/or splitting of minerals in water, etc.

For example, suitable paper compositions are described in Kirk-Othmer Encyclopedia of Chemical Technology 3rd Ed., Vol. 16, p768+ the relevant portions of which are incorporated by reference. Other suitable components are described in the following passages from Kirk-Othmer 3rd Ed.: paint compositions Vol. 16, p742+, oil drilling fluid Vol. 23, p948+, water treatment, Vol. 7, p 845+, detergents, Vol. 22, p332+, cosmetics, Vol. 7, p143+, inks Vol. 13, p374+, and leather emulsions Vol. 8, p925+ each relevant passage is hereby incorporated by reference.

This specific viscosity of the acrylic polymers and/or copolymers, symbolized by the letter "$\eta$," is determined in the following way.

A solution of the polymerization product is prepared in such a way that it corresponds to 2.5 g of dry polymer and to 50 ml of a 60 g/l solution of sodium chloride.

Next, a capillary viscosimeter with a Baume constant of 0.000105 placed in a bath thermostat-controlled to 25° C. is used to measure the flow time of a given volume of the aforementioned solution containing the acrylic polymer and/or copolymer, and the flow time of the same volume of aqueous solution of sodium chloride from which said polymer and/or copolymer is absent. The viscosity "$\eta$" can then be calculated by means of the following equation.

$$\eta = \frac{\text{(flow time of the polymer solution)} - \text{(flow time of the NaCl solution)}}{\text{flow time of the NaCl solution}}$$

The capillary tube is generally chosen so that the flow time of the NaCl solution not containing the polymer and/or copolymer, will be approximately 90 to 100 seconds, thus giving very accurate specific viscosity measurements.

These acrylic and/or vinyl polymers and/or copolymers according to the invention may also be treated using any conventional means to isolate them as a fine powder.

In practice, biodegradability is measured using the modified Sturm test, as described in the Official Journal of the European Community, No. L251 dated Sep. 19, 1984, and in the Guidelines of the OECD (organization for Economic Cooperation and Development), No. 301B dated May 12, 1981. This biodegradability, expressed as a percent, actually represents the amount of $CO_2$ that this substance can produce over a period of 36 days, as calculated based on its carbon content. Before undertaking these measurements, it is necessary to prepare the different test components, i.e.:

- a barium hydroxide solution ($Ba(OH)_2.8H_2O$), in order to trap and titrate the amount of $CO_2$, produced during the duration of the test;
- an inoculum used to inoculate the micro-organisms taken from sludges activated and controlled by the standard substance, in the present instance a 20 mg/l sodium acetate solution;
- the sample of the substance to be tested and the test medium.

In fact, the medium is composed of various reagent solutions, called stock solutions, which are made from high-quality water, i.e., distilled water containing no toxic substances (especially copper) and having a low carbon content (0.5 mg (TOC/l) (TOC=Total Organic Carbon) and a resistivity greater than, or equal to, 18 $M\Omega/cm$. For every liter of high-quality water, this medium contains:

- 4 ml of a ferric chloride solution obtained by dissolving 0.25 g of $FeCl_3.6H_2O$ in a liter of high-quality water;
- 1 ml of a magnesium sulfate solution obtained by dissolving 22.50 g of $MgSO_4.7H_2O$ in a liter of high-quality water;
- 1 ml of a calcium chloride solution obtained by dissolving 27.50 g of anhydrous $CaCl_2$ in a liter of high-quality water;
- 2 ml of a phosphate buffer solution obtained by dissolving 8.50 g of potassium dihydrogenophosphate ($KH_2PO_4$), 21.75 g of dipotassium hydrogenophosphate ($K_2HPO_4$), 33.40 g of dehydrate disodium hydrogenophosphate ($Na_2HPO_4.2H_2O$), and 1.70 g of ammonium chloride ($NH_4Cl$) in a liter of high-quality water;
- 1 ml of an ammonium sulfate solution obtained by dissolving 40 g of $(NH_4)_2SO_4$ in a liter of high-quality water.

Once these dissolutions have been made for three liters of reactive medium, the inoculum must be prepared. The inoculum used comes from activated sludges freshly collected from a sewage purification plant in good working condition. This plant must not treat industrial effluents, unless the quantities treated are negligible (approximately 10%).

When received at the laboratory, the activated sludges are aerated for four hours. Next, 500 ml of the suspension are collected and homogenized for two minutes at average speed using a magnetic stirring apparatus, before being decanted for $\frac{1}{2}$ hour.

If the floating material still contains an appreciable quantity of solid sludge particles after 30 minutes, it can either be left to decant for another 30 to 60 minutes, or it can be treated so as to produce a better decantation product.

The floating material must be left to decant so as to have available a sufficient volume to seed an inoculum in the proportion of 1% per $CO_2$-determination flask. It is also necessary not to carrying along solid sludge particles, which might falsify the measurement of $CO_2$ production.

It is useless to count in the floating fraction in order to determine the number of micro-organisms. The inoculum must generally contain $10^6$ to $20 \times 10^6$ units or colonies per ml. The inoculum must be used the same day it is prepared.

Once all of this had been accomplished, one need only add, to three different carboys, a control not containing any substance to be studied, a concentration of the substance to be studied (10 mg/l), and a comparison substance (sodium acetate) whose biodegradability must be greater than 60%, 2470 ml of high-quality water, and each of the stock solutions in a quantity corresponding to three liters of high-quality water and 30 ml of inoculum. The mixture is then aerated by air bubbling in the absence of $CO_2$ (after immersion in a barium hydroxide bath) for 24 hours before beginning the test.

The barium hydroxide solution is passed through filter paper and stored in an air-sealed place to prevent any $CO_2$ absorption.

The test begins after 24 hours of bubbling, by adding to each of the carboys containing the aerated mixture:
- some of the substance to be analyzed, in a concentration of 10 mg/l;
- some of the comparison substance, in a concentration of 20 mg/l;
- nothing further is added, so as to create a control.

The $CO_2$ produced in each carboy reacts with the barium hydroxide. The quantity of $CO_2$ produced is determined by titration of the remaining $Ba(OH)_2$ using 0.05N HCl. To that end, the $CO_2$-absorbing bottle nearest to the carboy is periodically disconnected (every two or three days).

After removing the bottles closest to the carboys, the $Ba(OH)_2$ is treated with 0.05N HCl, using phenolphthalein as an indicator.

The two remaining absorbing bottles are brought closer to the carboy while shifting them by one position, and, after off-line feeding, a new absorbing bottle containing 100 ml of a live 0.025N $Ba(OH)_2$ solution is added. Titrations are performed as needed (prior to the appearance of a $BaCO_3$ precipitate in the second trap, after that of the NaOH in a concentration of 8N), or approximately every two days for the first ten days, then every five days up to the 36th day. The experiment ends when the plateau appears signalling the decomposition of the substance to be studied.

On the 35th day, the pH of the solutions contained in the carboys is measured once again, and 1 ml of concentrated HCl is added to each carboy in order to eliminate the inorganic carbonate. The carboys are aerated overnight, and samples are collected from each of them in order to determine the dissolved organic carbon (DOC), whose action over the elapsed period is recorded solely for informational purposes. Titration is performed on the 36th day.

Having generally described this invention, a further understanding can be obtained by reference to certain specific examples which are provided herein for purposes of illustration only and are not intended to be limiting unless otherwise specified.

Example 1

This example involves measurement of the biodegradability of the same polyacrylic acid, which is neutralized by different ions.

Test No. 1 illustrating prior art indicates the biodegradability of a sodium polyacrylate which is 100% neutralized and has a specific viscosity of 0.54.

Test No. 2 illustrating the invention gives the biodegradability of a mixed sodium and magnesium polyacrylate obtained by complete neutralization carried out in such a way that 50% of the active acid sites are neutralized by sodium and 50% by magnesium. This polyacrylate has a specific viscosity of 0.54.

Test No. 3 illustrating the invention gives the biodegradability of a mixed sodium and magnesium polyacrylate obtained by neutralization carried out in such a way that 25% of the active acid sites are neutralized by sodium and 75% by magnesium. This polyacrylate has a specific viscosity of 0.54.

For all of these tests, the micro-organism source came from activated sludges collected at the Pierre Benite (France) purification plant. The working conditions were those mentioned above.

All of the results are recorded in Table 1.

TABLE 1

| TEST NO. | NEUTRALIZATION | | Number of days | Biodegradability % |
|---|---|---|---|---|
| | Percentage of neutralized acids | Neutralizing Cation | | |
| 1* | 100 | Na | 36 | 43 |
| 2** | 50/50 | Na/Mg | 36 | 54 |
| 3** | 25/75 | Na/Mg | 36 | 65 |

*Prior Art
**Invention

A reading of Table 1 makes it possible to rveal the biodegradability differential between the polymer according to prior art and the polymer according to the invention.

In fact, in Test No. 1, the percentage of the theoretical quantity of $CO_2$ is 43% after 36 days, while that in Test No. 2 is 54% after 36 days and the percentage in Test No. 3 is 65% after 36 days.

Thus, only the polymers according to the invention, which are produced by neutralization of a polyacrylic acid using a neutralizing mixture containing magnesium ions, yield a biodegradability of more than 50% after a 36-day test.

Example 2

This examples involves measurement of the biodegradability of the same initial polyacrylic acid, which has a specific viscosity of 0.54 and is neutralized by proportions of magnesium reaching 88% of the active acid sites of the polymer.

Test No. 4 measures the biodegradability of a mixed sodium and magnesium polyacrylate neutralized in such a way that 70% of the active acid sites are neutralized by sodium and 30% by magnesium.

Test No. 5 measures the biodegradability of a mixed sodium and magnesium polyacrylate neutralized in such a way that 60% of the active acid sites are neutralized by sodium and 40% by magnesium.

Test No. 6 measures the biodegradability of a mixed sodium and magnesium polyacrylate neutralized in such a way that 50% of the active acid sites are neutralized by sodium, and 50% by magnesium.

Test No. 7 measures the biodegradability of a mixed sodium and magnesium polyacrylate neutralized in such a way that 35% of the active acid sites are neutralized by sodium, and 65% by magnesium.

Test No. 8 measures the biodegradability of a mixed sodium and magnesium polyacrylate neutralized in such a way that 25% of the active acid sites are neutralized by sodium, and 75% by magnesium.

Test No. 9 measures the biodegradability of a mixed sodium and magnesium polyacrylate neutralized in such a way that 12% of the active acid sites are neutralized by sodium and 88% by magnesium.

Test No. 10 measures the biodegradability of a polyacrylate in which 50% of the active acid sites are neutralized by magnesium ions.

Test No. 11 measures the biodegradability of a polyacrylate having the same specific viscosity, i.e., 0.54, in which 75% of the active acid sites are neutralized by magnesium ions.

The micro-organism source and the testing conditions are identical to those in Example 1.

All of the results are recorded in Table 2.

TABLE 2

| TEST NO. | NEUTRALIZATION | | Number of days | Biodegradability % |
|---|---|---|---|---|
| | Percentage of neutralized acids | Neutralizing Cation | | |
| 4 | 70/30 | Na/Mg | 36 | 44 |
| 5 | 60/40 | Na/Mg | 36 | 51 |
| 6 | 50/50 | Na/Mg | 36 | 54 |
| 7 | 35/65 | Na/Mg | 36 | 57 |
| 8 | 25/75 | Na/Mg | 36 | 65 |
| 9 | 12/88 | Na/Mg | 36 | 71 |
| 10 | 50 | Mg | 36 | 52 |
| 11 | 75 | Mg | 36 | 63 |

A reading of the results recorded in Table 2 reveals that, in Tests Nos. 5 to 11, the percentage of the theoretical quantity of $CO_2$ exceeds 50%, while, in Test No. 4, it is only 44%.

Thus, the use of Mg ions to produce a percentage of neutralization of the active acid sites of between 35% and 90% gave a polymer according to the invention having an improved biodegradability of more than 50% after 36 testing days. Optimal results were achieved for a polymer according to the invention, in which 75% of the active acid sites were neutralized by magnesium ions, and 25% by sodium ions; and better still, when 88% of the active acid sites were neutralized by magnesium ions and 12% by sodium ion.

Example 3

This example involves measurement of the biodegradability of polyacrylic acids having different molecular weights.

Test No. 12 measured the biodegradability of a mixed sodium and magnesium polyacrylate obtained through complete neutralization, so that 50% of the active acid sites were neutralized by sodium ions and 50% by magnesium ions; the mixed polyacrylate had a specific viscosity of 0.3.

Test No. 13 was identical to Test No. 2 (specific viscosity=0.54).

Test No. 14 measured the biodegradability of a mixed sodium and magnesium polyacrylate obtained through complete neutralization, so that 50% of the active acid sites were neutralized by sodium ions, and 50% by magnesium ions. This polyacrylate had a specific viscosity of 5.0.

Test No. 15 measured the biodegradability of a mixed sodium and magnesium polyacrylate obtained through complete neutralization, so that 25% of the active acid sites were neutralized by sodium ions and 75% by magnesium ions. This polyacrylate had a specific viscosity of 0.3.

Test No. 16 was identical to Test No. 3 (specific viscosity 0.54).

Test No. 17 measured the biodegradability of a mixed sodium and magnesium polyacrylate obtained through complete neutralization, so that 25% of the active acid sites were neutralized by sodium ions and 75% by magnesium ions. It had a specific viscosity of 5.0.

The micro-organism source and test working conditions were identical to those in Example 1.

All of the results are recorded in Table 3.

TABLE 3

| TEST NO. | NEUTRALIZATION | | Specific viscosity | Number of days | Biodegradability % |
|---|---|---|---|---|---|
| | Percentage of neutralized acids | Neutralizing Cation | | | |
| 12 | 50/50 | Na/Mg | 0.3 | 36 | 57 |
| 13 | 50/50 | Na/Mg | 0.54 | 36 | 54 |
| 14 | 50/50 | Na/Mg | 5.0 | 36 | 51 |
| 15 | 25/75 | Na/Mg | 0.3 | 36 | 77 |
| 16 | 25/75 | Na/Mg | 0.54 | 36 | 65 |
| 17 | 25/75 | Na/Mg | 5.0 | 36 | 59 |

A reading of the results in Table 3 reveals that, whatever the specific viscosity, i.e., the molecular weight of the polymer, the polymers according to the invention, which are partially neutralized by magnesium ions, have an enhanced biodegradability exceeding 50% after 36 testing days.

Example 4

This example involved measurement of the biodegradability of other polymers, whether neutralized or not by magnesium ions.

Test No. 18 measured the biodegradability of a polymer obtained by polymerization and grafting acrylic acid on a polyethylene glycol which had a molecular weight of 3400 and was 100% neutralized by sodium, as described in Example 1 in Patent No. EP0429307.

Test No. 19 measured the biodegradability of the same polymer as that in Test No. 18, but which, in this case, was 100% neutralized by a mixture corresponding to 50% neutralization using sodium and 50% neutralization using magnesium.

Test No. 20 measured biodegradability of the same polymer as that in Test No. 18, but which, in this case, was 100% neutralized by a mixture corresponding to 25% neutralization using sodium 75% neutralization using magnesium.

The micro-organism source and the test working conditions were identical to those in Example 1.

All of the results were recorded in Table 4.

TABLE 4

| TEST NO. | NEUTRALIZATION | | Number of days | Biodegradability % |
|---|---|---|---|---|
| | Percentage of neutralized acids | Neutralizing Cation | | |
| 18* | 100 | Na | 36 | 48 |
| 19** | 50/50 | Na/Mg | 36 | 61 |
| 20** | 25/75 | Na/Mg | 36 | 68 |

*Prior art
**Invention

A reading of the results in Table 4 reveals the biodegradability differential between the polymer according to prior art and those according to the invention.

In fact, in Test No. 18, biodegradability was 48% after 36 testing days, while the biodegradability in Test No. 19 was 61% after 36 testing days and, in Test No. 20, 68% after 36 testing days.

Thus the use, according to the invention, of a neutralizing agent containing the magnesium ion gives polymers possessing improved biodegradability exceeding 50% after 36 testing days.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A water-soluble biodegradable polymer comprising: a polymer selected from the group consisting of acrylic polymer, vinyl polymer and copolymers thereof
   wherein the active acid sites of said polymer are completely or partially neutralized by at least one neutralizing agent containing magnesium ions, such that the degree of neutralization of said active acid sites by means of magnesium ions ranges between 35 and 90%,
   wherein biodegradability as measured using the modified Sturm test is greater than 50% at the end of 36 days.

2. The water-soluble biodegradable polymer of claim 1, wherein the degree of neutralization of the active acid sites by means of magnesium ions ranges between 35% and 60%.

3. The water-soluble biodegradable polymer of claim 1, wherein the degree of neutralization of the active acid sites by means of magnesium ions ranges between 60% and 90%.

4. The water-soluble biodegradable polymer of claim 1, wherein up to 65% of the active acid sites are neutralized by at least one neutralizing agent containing monovalent ions.

5. The water-soluble biodegradable polymer of claim 2, wherein up to 65% of the active acid sites are neutralized by at least one neutralizing agent containing monovalent ions.

6. The water-soluble biodegradable polymer of claim 3, wherein up to 40% of the active acid sites are neutralized by at least one neutralizing agent containing monovalent ions.

7. The water-soluble biodegradable polymer of any one of claims 4-6, wherein said monovalent ions of the neutralization agent is selected from the group consisting of sodium, potassium, lithium, ammonium, aliphatic primary amine, aliphatic secondary amine, and aliphatic tertiary amine, cyclic primary amine, cyclic secondary amine, cyclic tertiary amine, hydroxy substituted aliphatic primary amine, hydroxy substituted aliphatic secondary amine and hydroxy substituted aliphatic tertiary amine.

8. The water-soluble biodegradable polymer of any one of claims 4 or 5, wherein 50% of the active acid sites of said polymer are neutralized using a neutralizing agent containing magnesium ions, and 50% using a neutralizing agent containing monovalent sodium ions.

9. The water-soluble biodegradable polymer of any one of claims 4 or 6, wherein 75% of the active acid sites of said polymer are neutralized using a neutralizing agent containing magnesium ions, and 25% using a neutralizing agent containing monovalent sodium ions.

10. The water-soluble biodegradable polymer of any one of claims 4 or 6, wherein 88% of the active acid sites of said polymer are neutralized using a neutralizing agent containing magnesium ions, and 12% using a neutralizing agent containing monovalent sodium ions.

11. The water-soluble biodegradable polymer of any one of claims 4-6, wherein said polymer has a specific viscosity of at most 25, and preferably at most 10.

12. The water-soluble biodegradable polymer of claim 11, wherein said polymer is in solution.

13. The water-soluble biodegradable polymer of claim 11, wherein said polymer is a powder.

14. The water-soluble biodegradable polymer of claim 1, wherein said polymer is obtained by polymerizing acrylic monomers, vinyl monomers or a mixture thereof.

15. The water-soluble biodegradable polymer of claim 1, wherein said polymer is obtained by treating acrylic polymer, vinyl polymer, or acrylic/vinyl polymer by static or dynamic procedures in at least one polar solvent.

16. The water-soluble biodegradable polymer of claim 1, wherein said polymer is obtained by grafting acrylic monomers, vinyl monomers as a mixture thereof onto a polyalkylene glycol-based substrate.

17. A process for imparting to water-soluble polymers enhanced biodegradability, as measured by the modified Sturm test, exceeding 50% after 36 days, comprising complete or partial neutralization of the active acid sites of said polymers, using an agent containing magnesium ions.

18. A composition comprising:
   i) the water-soluble biodegradable polymer of claim 1; and
   ii) at least one additive selected from the group consisting of solvents, pigments, fillers, dyes, and surfactants.

* * * * *

UNITED STATES PATENT AND TRADEMARK OFFICE
CERTIFICATE OF CORRECTION

PATENT NO. : 5,278,248
DATED : JANUARY 11, 1994
INVENTOR(S) : JEAN-BERNARD EGRAZ ET AL

It is certified that error appears in the above-identified patent and that said Letters Patent is hereby corrected as shown below:

Column 1, line 16, "EP0429307 and EP0430574)" should read --(EP0429307 and EP0430574)--.

Column 2, line 17, "As suitable" should read --A suitable--.

Column 4, line 56, "not to carrying" should read --not to carry--.

Column 6, line 34, "This examples" should read --This example--.

Column 8, line 37, "sodium 75%" should read --sodium, 75%--.

Signed and Sealed this

Twenty-eight Day of March, 1995

Attest:

BRUCE LEHMAN

Attesting Officer     Commissioner of Patents and Trademarks